United States Patent
Gangjee et al.

(10) Patent No.: US 9,446,045 B2
(45) Date of Patent: *Sep. 20, 2016

(54) METHODS OF USING SELECTIVE CHEMOTHERAPEUTIC AGENTS FOR TARGETING TUMOR CELLS

(71) Applicants: Aleem Gangjee, Allison Park, PA (US); Larry H. Matherly, Farmington Hills, MI (US)

(72) Inventors: Aleem Gangjee, Allison Park, PA (US); Larry H. Matherly, Farmington Hills, MI (US)

(73) Assignees: Duquesne University of the Holy Ghost, Pittsburgh, PA (US); Wayne State University, Detroit, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/592,149

(22) Filed: Jan. 8, 2015

(65) Prior Publication Data
US 2015/0126536 A1 May 7, 2015

Related U.S. Application Data

(62) Division of application No. 14/020,136, filed on Sep. 6, 2013, now Pat. No. 8,952,019, which is a division of application No. 13/561,657, filed on Jul. 30, 2012, now Pat. No. 8,552,014, which is a division of application No. 11/820,872, filed on Jun. 21, 2007, now Pat. No. 8,258,143.

(60) Provisional application No. 60/816,931, filed on Jun. 28, 2006.

(51) Int. Cl.
*A61K 31/519* (2006.01)
*C07D 487/04* (2006.01)

(52) U.S. Cl.
CPC .......... *A61K 31/519* (2013.01); *C07D 487/04* (2013.01)

(58) Field of Classification Search
None
See application file for complete search history.

(56) References Cited

U.S. PATENT DOCUMENTS

| 5,939,420 | A | 8/1999 | Gangjee | |
|---|---|---|---|---|
| 7,981,902 | B2 * | 7/2011 | Gangjee | A61K 31/535 514/265.1 |
| 8,258,143 | B2 * | 9/2012 | Gangjee | C07D 487/04 514/265.1 |
| 8,552,014 | B2 * | 10/2013 | Gangjee | C07D 487/04 514/265.1 |
| 8,952,019 | B2 * | 2/2015 | Gangjee | C07D 487/04 514/265.1 |

FOREIGN PATENT DOCUMENTS

EP 0438261 7/1991

OTHER PUBLICATIONS

National Library of Medicine—Medical Subject Headings, 2007. Pemetrexed, Electronic Resource [http://www.nim.nih.gov/cgi/mesh/2007/MB_cgi].
Hanauske et al., "Pemetrexed Disodium: A Novel Antifolate Clinically Active Against Multiple Solid Tumors", The Oncologist, 2001, 6: 363-373.
Gangjee et al., "Synthesis of Classical, Three-Carbon Bridged 5 Substituted Furo[2,3-d]pyrimidine and 6-Substituted Pyrrolo[2,3-d]pyrimidine Analogues as Antifolates", J. Med. Chem. 2004, 47, 6893-6901.
Gangjee et al., "Synthesis of Classical, Four-Carbon Bridged 5 Substituted Furo[2,3-d]pyrimidine and 6-Substituted Pyrrolo[2,3-d]pyrimidine Analogues as Antifolates", J. Med. Chem. 2005, 5329-5336.

* cited by examiner

*Primary Examiner* — Anna Pagonakis
(74) *Attorney, Agent, or Firm* — Buchanan Ingersoll & Rooney PC; Craig G. Cochenour

(57) ABSTRACT

A method for treating cancer tumors, particularly ovarian cancer tumors, is described, where fused cyclic pyrimidine having a cancer treating ability is selectively delivered to an FR expressing cancerous tumor.

25 Claims, 1 Drawing Sheet

METHODS OF USING SELECTIVE CHEMOTHERAPEUTIC AGENTS FOR TARGETING TUMOR CELLS

CROSS-REFERENCE TO RELATED APPLICATIONS

This is a divisional patent application of and claims the benefit of priority of co-pending prior U.S. patent application Ser. No. 14/020,136, filed on Sep. 6, 2013, which is a divisional application of and claims the benefit of U.S. patent application Ser. No. 13/561,657, filed on Jul. 30, 2012, now U.S. Pat. No. 8,552,014 B2, granted Oct. 8, 2013, which is a divisional application of and claims the benefit of U.S. patent application Ser. No. 11/820,872, filed Jun. 21, 2007, now U.S. Pat. No. 8,258,143 B2, granted Sep. 4, 2012, which claims the benefit of U.S. Provisional Patent Application Ser. No. 60/816,931 filed Jun. 28, 2006 (now expired), the disclosure of each of which are incorporated herein by reference.

GOVERNMENT CONTRACT

This invention was supported in part by the National Institutes of Health, U.S. Department of Health and Human Services under Contract No. CA 89300. The government has certain rights in the invention.

BACKGROUND OF THE INVENTION

1. Field of the Invention

The present invention relates to methods for providing selected chemotherapeutic agents which selectively target folate receptors (FR) of cancerous tumor cells and inhibit GARFTase contained in the cells, particularly types of ovarian cancer cells. Specifically, the present invention relates a method for the use of fused cyclic pyrrolo derivatives, particularly fused cyclic pyrimidines having a long chain $CH_2$ group between cyclic groups, which themselves selectively target folate receptors ("FR"), particularly FR-alpha of cancerous tumor cells. They also inhibit glycinamide ribonucleotide formyltransferace enzyme (GARFTase) in tumor cells, where the fused cyclic pyrimidines themselves are effective to selectively penetrate inside of the cancerous tumor cells.

2. Description of the Prior Art

Cancer chemotherapy agents as taught, for example in U.S. Pat. No. 5,939,420 (Gangjee), do not specifically selectively target cancer tumor cells but target both normal and tumor cells. This lack of selectivity for tumor cells results in cytotoxicity to the normal cells and is also one of the major causes of chemotherapeutic failure in the treatment of cancer. Further, advanced stage and platinum resistant tumors may be difficult to treat with traditional chemotherapeutic agents such as, but not limited to, carboplatin or paclitaxel (docitaxel). Other documents in this area include *J. Med. Chem.* 48 (16), 5329-5336, web release date Jul. 9, 2005 "Synthesis of Classical Four-Carbon Bridged 5-Substituted Furo-[2-3-d]-pyrimidine and 6-Substituted Pyrrolo-[2,3-d]-pyrimidine Analogues as Antifolates" by A. Gangjee et al.

As is known in the prior art, a type of folate receptor FR, FR-alpha, is overexpressed on a substantial amount of certain surfaces of a number of cancerous tumors including, but not limited to, ovarian, endometrial, kidney, lung, mesothelioma, breast, and brain tumors.

In most normal tissues, the FR-alpha is not present and the folic acid is not taken up by the normal cells by way of a reduced folate carrier system (RFC), thereby leading to selective uptake by tissues such as FR-alpha expressing ovarian tumors. In light of the specificity of folic acid, conjugates of folic acid have been used in the prior art to selectively deliver toxins, liposomes, imaging and cytotoxic agents to FR-alpha expressing tumors.

However, one of the major limitations of the foregoing, such as cytotoxic-folic acid conjugates, is that its use requires cleavage from the folic acid moiety to release the cytotoxic drug. Moreover, premature release of the cytotoxic agent during the transport before reaching the tumor destroys selectivity and thereby leads to undesired toxicity in normal cells. This is a very serious detriment scientifically and commercially.

Further, if the folic acid moiety of the cytotoxic-folic acid conjugate is difficult to cleave, then the anti-tumor activity is hindered as a result of the inability or reduced ability to release the cytotoxic agent. Accordingly, treatment of the tumor cells with the cytotoxic agent is either hindered or rendered nil as a result of the difficulty in cleaving the cytotoxic agent moiety from the folic acid-based conjugate.

In spite of the foregoing prior art, however, there remains a very real need for methods and compositions that selectively target FR-alpha of tumor cells.

An object of this invention is to provide methods for selectively targeting FR, particularly FR-alpha, of tumor cells with a cancer-treating agent, targeting the GARFTase enzyme.

In a related object, the method does not use conjugated compositions and does not need cleavage to release a cytotoxic drug.

In yet another related object, the method will allow penetration into the cancerous cells, expressing FR, that is, FR-alpha and/or FR-beta, but not into a cell using the reduced folate carrier system (RFC).

Another object of this invention is to provide effective delivery of a cancer treating agent to the cancerous tumor in the process of treating a patient.

Another object of this invention is to efficiently target a cancerous tumor.

Another object of this invention is to provide an essentially non-toxic method of treating a cancerous tumor.

SUMMARY OF THE INVENTION

The present invention has filled the above described need and satisfied the above objects by providing methods for selectively targeting FR of tumor cells with a cancer-treating agent. The term "FR" as used herein includes receptors selected from the group consisting of FR-alpha, FR-beta and mixtures thereof. Folate receptors of the FR-beta-type are expressed on surfaces of myeloid leukemia cancerous tumors. In a preferred embodiment, the compositions and methods selectively target FR-alpha and FR-beta of cancerous tumor cells.

Very significantly, in the method, the cancer treating agent is not significantly taken up by a cell or tissue using the RFC system.

The cancer treating agent used in this method is a fused cyclic pyrimidine and is used to selectively target FR of ovarian tumors, advanced stage cancerous tumors that express FR receptors and drug-resistant tumors such as, but not limited to, those resistant to carboplatin, paclitaxel, and/or docitaxel. The receptors are preferably FR-alpha and beta types.

More specifically, the invention relates to a method of inhibiting GARFTase in a cancerous tumor of a patient comprising:

(a) providing a fused cyclic pyrimidine shown in FIGS. 1(a) and (b), where n=3-6 alkyl chain carbons between the major ring groups I and II;

(b) selectively delivering the fused cyclic pyrimidine alone to a FR cancerous tumor, where due to the use of long chain carbons (n=3-6), the fused cyclic pyrimidine targets primarily cancerous tumors which contain FR. The fused cyclic pyrimidine enters said cancerous tumors, acting as a cancer-treating agent itself, and inhibits GARFTase within the tumors. Here the fused cyclic pyrimidine functions as a substrate of folylpolyglutamate synthetase (FPGS) in the tumors therefore being trapped in the tumors.

The distance and orientation of the side chain p-aminobenzoyl-L-glutamate moiety with respect to the pyrimide ring are extremely important for biological activity; hence, n=3-6 in FIGS. 1(a) and (b) provide surprisingly unique results. Here the fused cyclic pyrimidine acts as carrier, targeting and cancer treating agent. No fusing of a separate cancer treating agent to the fused cyclic pyrimidine is required.

The invention will be more fully understood by review of the drawings in view of the following detailed description of the invention, and the claims appended thereto.

DESCRIPTION OF THE PREFERRED EMBODIMENTS

Figure 1A:
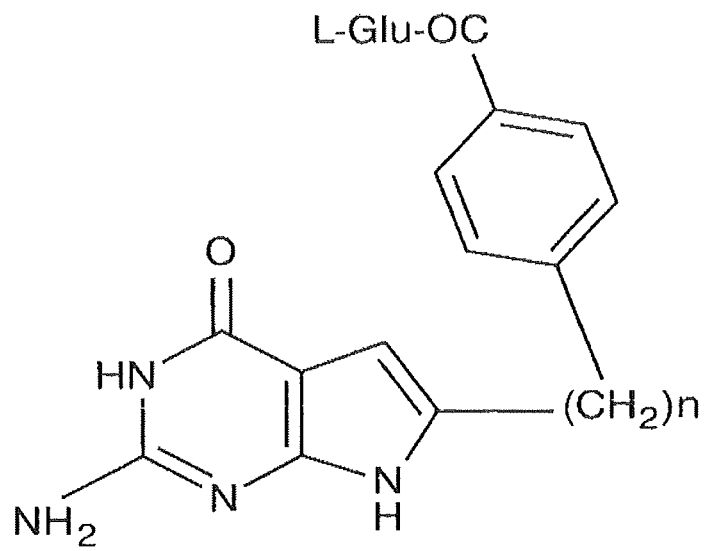
FIG. 1(a) shows a general chemical formula for the fused cyclic pyrimide used in the method of this invention, where "L-Glu" is a L-Glutamic Acid (or L-Glutamate) group based on an amino acid having the formula $CH_1H_9-NH_4$.

As used herein, "tumor" refers to an abnormal growth of cells or tissues of the malignant type, unless otherwise specifically indicated and does not include a benign type tissue. The "tumor" may be comprised of at least one cell and/or tissue. The term "inhibits or inhibiting" as used herein means reducing growth or replication. As used herein, the term "cancer" refers to any type of cancer, including ovarian cancer, leukemia, lung cancer, colon cancer, CNS cancer, melanoma, renal cancer, prostate cancer, breast cancer, and the like. As used herein, the term "patient" refers to members of the animal kingdom including but not limited to human beings. The fused cyclic pyrimidine of the invention has five unique properties: 1) inhibition of PR-alpha and beta cancerous tumors; 2) a lack of appreciable uptake by the RFC; 3) ability to act itself as a cancer treating agent; 4) ability to penetrate cancerous tumors having folate receptors; 5) ability to function as substrate for folylpolyglutamate synthetase (FPGS) thereby being trapped in the tumor cells and 6) inhibition of GARFTase. The fused cyclic pyrimidine of this invention targets cancers with certain receptors and is practically non-toxic. These fused cyclic pyrimidines are taken into the tumor cells, via the FR selectivity.

Selectivity of the fused cyclic pyrimidine is made possible since most normal cells do not have receptors of the FR type. Further, when expressed, FR-alpha is the most widely expressed receptor isoform in adult tissue. FR-alpha occurs at the apical (i.e., luminal) surface of epithelial cells where it is not supplied by folate in the circulation.

Embodiments of the invention follow. The fused cyclic pyrimidine where n=3-6 has an affinity for receptors such as FR or FR-alpha. These receptors are mainly present on the surface of cancerous tumor cells, and not other types of folate transport systems that are more predominant on the surface of normal cells. In other words, the fused cyclic pyrimidine is preferably not taken up to an appreciable degree by the reduce folate carrier (RFC) system. FR-alpha are generally not expressed in normal cells. The fused cyclic pyrimidine stays inside of the cancerous tumor cell for an effective amount of time to kill the tumor cell. This occurs by way of polyglutamylation and the multi ionic form of the fused cyclic pyrimidine itself inside of the tumor cell. The fused cyclic pyrimidine also disrupts the replication process of the cancerous tumor cell, thereby inhibiting the growth of FR-alpha expressing cancerous tumor cells.

The foregoing embodiments are enabled by way of a glycinamide ribonucleotide formyltransferase ("GARFTase") inhibition. GARFTase is an enzyme which is essential to DNA synthesis of normal and cancerous tumor cells.

Here the fused cyclic pyrimidine itself has a high affinity for the FR-alpha receptors which are overexpressed on the surface of cancerous tumor cells. The fused cyclic pyrimidine passing into the cancerous tumor cells inhibits GARFTase activity and inhibits DNA synthesis. Accordingly, the targeted tumor cells which overexpress FR-alpha are prevented from replicating and are killed.

In a preferred embodiment, the fused cyclic pyrimidine has a significantly greater affinity tor FR-alpha expressing cells compared with cells that do not express FR-alpha. Accordingly, the fused cyclic pyrimidine would have a greater affinity for cells which overexpress FR-alpha (i.e., certain cancerous tumor cells as described in more detail above), but also an affinity for FR-beta cells.

At present, there are no other agents known with the above-described four attributes in a single chemotherapy agent and therefore the presently invented compositions are felt to be unique with regard to other GARFTase or FR-alpha targeting agents, including any known agent in clinical or investigational use.

EXAMPLES

This example relates to just one of the many possible targets, ovarian cancer.

Materials and Methods

Pyrrolo derivatives (fused cyclic pyridimines), such as shown in FIGS. 1(a) and (b) (n=3 or 4) AAG366 and AAG344 respectively. These compounds were designed using molecular modeling, superimposition and/or docking onto an X-ray crystal structure of GARFTase while maintaining FR-alpha targeting ability using structure based design.

Testing.

AAG366 and AAG344 were evaluated in two assays, in vitro and in vivo. The following four properties were considered:

Single digit nanomolar inhibition of FR-alpha expressing tumor cells. Substrate for FPGS (attributes of AAG366 FIG. 1, where n=3 and AAG344 where n=4).

Method of selectively delivering a cytotoxic GARFTase inhibitor to tumor cells. Greater number of FR-alpha expressed on advanced and platinum resistant tumors.

Method of selectively increasing the cytotoxic agent concentration in the tumors, affording selective delivery of AAG366 FIG. 1.

Method of inhibiting advanced stage and resistant tumors without major toxicity.

Figure 1B:
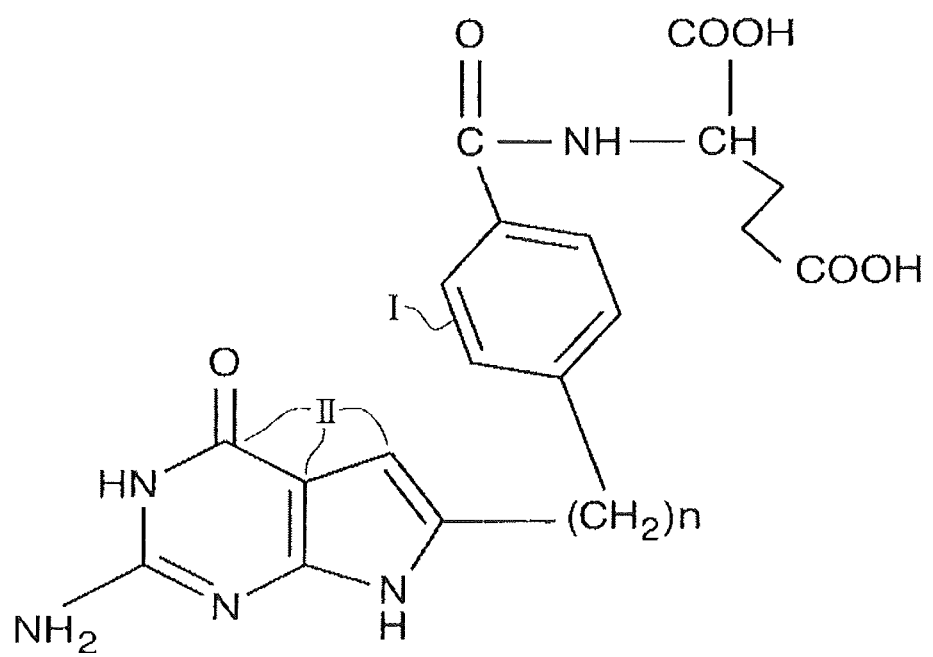
FIG. 1(b) shows another description of the formula of FIG. 1(a), where n is the total number of $CH_2$ groups between the major cyclic/ring groups, such groups shown as I and II.

Recently discovered compounds AAG366 (n=3) and AAG344 (n=4), FIGS. 1(a) and 1(b), potently inhibit the growth of FR-alpha expressing KB tumor cells with $IC_{50}$=2.5 and 2.9 nM, respectively. In addition, these compounds are nanomolar inhibitors of glycinamide ribonuelcotide formyltransferase (GARFTase), a critical enzyme in purine nucleotide biosynthesis, and are not taken up by the RFC. Both these compounds are remarkably selective for tumor cells expressing FR-alpha. AAG344 is greater than 345-fold more inhibitory to tumor cells expressing the FR-alpha compared to cells that do not. AAG366 (n=3) is 100-180 fold more inhibitory.

AAG366, AAG344, the clinically used antifolates methotrexate, pemetrexed, ratitrexed, as well as the most important GARFTase inhibitor DDATHF (Lometrexol) were evaluated. All of the aforementioned compounds were less potent against FR-alpha expressing RT16 cells compared with AAG366 and AAG344 and none showed selectivity for the FR-alpha expressing RT16 cells over RFC expressing pc43-10 cells. Unlike AAG366 and AAG344, all of these analogs inhibited the RFC expressing pc43-10 cells with greater potency (methotrexate, pemetrexed, ratitrexed) or equal potency (DDATHF) compared to the FR-alpha expressing RT16 cells (AAG366) or KB cells (AAG344) and were thus devoid of selectivity.

Research indicates that AAG366 and AAG344 are the only known compounds with these three attributes, i.e., 1) GARFTase inhibition; 2) single digit nanomolar FR-alpha expressing tumor cell inhibition; and 3) a 100 to >345-fold selectivity for FR-alpha expressing cells over cells that lack the FR-alpha, including those with the RFC. These three important attributes make AAG366 and AAG344 particularly attractive as antitumor agents. Such novel agents could be used alone or in combination with other chemotherapeutic agents to afford synergistic effects against tumors with reduced toxicity and thus address the major obstacle of toxicity in cancer chemotherapy.

Impact, for Example with Ovarian Tumors:

The compound indicated in FIGS. 1(a) and (b) (n=3 or 4) specifically targets the FR-alpha and is not taken up by the RFC in normal cells. Since 90-95% of ovarian cancers overexpress the FR-alpha, one would expect that these compounds will be highly selective for ovarian cancer as well as ovarian cancers resistant to one or both of the most widely used chemotherapeutic agents, carboplatin or paclitaxel (docitaxel). The mechanism of action of the aforementioned agents is different from the GARFTase inhibitors of this invention and selectivity, if any of these prior reagents, is not based on FR-alpha. The use of FR-alpha targeting GARFTase agents could radically impact the course of treatment outcomes for ovarian cancer because of their selectivity for FR-alpha expressing ovarian tumor cells that could result in "cures" without toxicity to host cells. Metastasized ovarian cancer cells in the peritoneal cavity also over express FR-alpha and would be selectively targeted by our analogs.

Data has shown that compounds of FIGS. 1(a) and (b) (n=4) at high extracellular levels is able to diffuse through plasma membranes, and had increased inhibitory potency against CCRF-CEM cell growth in culture compared to compounds where n=2.

What is claimed is:

1. A method for inhibiting GARFTase in cancerous tumors of a patient comprising:
   a) providing a fused cyclic pyrimidine having the chemical formula:

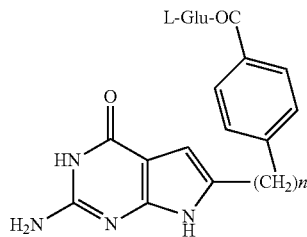

where n=5 or 6;
   b) selectively delivering the fused cyclic primidine alone to brain cancerous tumors, where the fused cyclic pyrimidine due to the of $CH_2$ chains, where n=5 or 6,targets primarily FR-expressing cancerous tumors; and
   c) passing of the fused cyclic pyrimidine into said cancerous tumors where the fused cyclic pyrimidine itself acts as a cancer treating agent and inhibits GARFTase within the tumors.

2. The method of claim 1, wherein said fused cyclic pyrimidine is selective for receptors selected from the group consisting of FR-alpha, FR-beta and mixtures thereof, associated with expressing cancerous tumors.

3. The method of claim 1, wherein said fused cyclic pyrimidine is selective for FR-alpha expressing cancerous cells.

4. The method of claim 1, wherein said fused cyclic pyrimidine is not significantly taken up by a tissue or a cell using the reduced folate carrier system (RFC system).

5. The method of claim 1, wherein the fused cyclic pyrimidine functions as a substrate of folylpolyglutamate synthetase (FPGS) in the tumors, thereby being trapped in the tumors.

6. The method of claim 1, wherein the fused cyclic pyrimidine stays inside the cancerous tumor for an effective amount of time to kill the tumors by way of polyglutamylation and the multi ionic form of the fused pyrimidine itself.

7. The method of claim 1, wherein said fused cyclic pyrimidine requires no separate cancer treating agent or conjugation to a separate cytotoxic agent.

8. The method of claim 1, wherein said fused cyclic pyrimidine targets at least one advanced stage cancerous tumor.

9. The method of claim 1, wherein said fused cyclic pyrimidine targets at least one platinum resistant cancerous tumor.

10. The method of claim 1, wherein said fused cyclic pyrimidine targets at least one carboplatin resistant cancerous tumor.

11. The method of claim 1, wherein said fused cyclic pyrimidine targets at least one paclitaxel resistant cancerous tumor.

12. The method of claim 1, wherein said fused cyclic pyrimidine targets at least one docetaxel resistant cancerous tumor.

13. The method of claim 1, wherein said fused cyclic pyrimidine is polyglutamylated by folypoly-gamma glutamate synthetase.

14. The method of claim 1, wherein said fused cyclic pyrimidine is tolerable in vivo.

15. The method of claim 1, wherein n=5 in the chemical formula.

16. The method of claim 1, wherein n=6 in the chemical formula.

17. A method for inhibiting GARFTase in cancerous tumors comprising:
   a) providing a fused cyclic pyrimidine having a cytotoxic capability having the chemical formula:

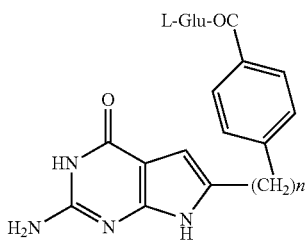

where n=5 or 6;
   b) selectively targeting a folate receptor alpha (FR-alpha) expressing brain cancerous tumor, with said fused cyclic pyrimidine, wherein said cancerous tumor expresses a plurality of FR receptors;
   c) selectively delivering said fused cyclic pyrimidine to said cancerous tumor;
   d) passing of the fused cyclic pyrimidine into said cancerous tumor;
   e) retaining said fused cyclic pyrimidine in said cancerous tumor for a sufficient time for lysing of said cancerous tumor; and
   f) lysing of said cancerous tumor by said fused cyclic pyrimidine binding with said GARFTase to inhibit DNA replication of said cancerous tumor.

18. The method of claim 17, wherein said fused cyclic pyrimidine is selective for receptors selected from the group consisting of FR-alpha, FR-beta and mixtures thereof, associated with expressing cancerous tumors.

19. The method of claim 17, wherein the fused cyclic pyrimidine stays inside the cancerous tumor for an effective amount of time to kill the tumor by way of polyglutamylation and the multi ionic form of the fused pyrimidine itself.

20. The method of claim 17, wherein said fused cyclic pyrimidine requires no separate cancer treating agent or conjugation to a separate cytotoxic agent.

21. The method of claim 17, wherein said fused cyclic pyrimidine is tolerable in vivo.

22. The method of claim 17, wherein the fused cyclic pyrimidine targets primarily FR-alpha expressing cancerous tumors.

23. The method of claim 22, wherein said fused cyclic pyrimidine requires no separate cancer treating agent or conjugation to a separate cytotoxic agent.

24. The method of claim 17, wherein n=5 in the chemical formula.

25. The method of claim 17, wherein n=6 in the chemical formula.

* * * * *